(12) United States Patent
Rubin

(10) Patent No.: US 11,547,669 B2
(45) Date of Patent: Jan. 10, 2023

(54) INDIGENOUS AND IMPROVED BACTERIALLY FERMENTED CBD, CBG AND RELATED CANNABINOID ORAL DOSAGE FORMS

(71) Applicant: Beyond Hemp, LLC, Summertown, TN (US)

(72) Inventor: Jordan Seth Rubin, College Grove, TN (US)

(73) Assignee: Fermented Farmer, LLC., Summertown, TN (US)

( * ) Notice: Subject to any disclaimer, the term of this patent is extended or adjusted under 35 U.S.C. 154(b) by 219 days.

(21) Appl. No.: 16/861,679

(22) Filed: Apr. 29, 2020

(65) Prior Publication Data

US 2021/0106533 A1    Apr. 15, 2021

Related U.S. Application Data

(63) Continuation-in-part of application No. 16/781,489, filed on Feb. 4, 2020.

(60) Provisional application No. 62/912,930, filed on Oct. 9, 2019.

(51) Int. Cl.
| | | |
|---|---|---|
| *A61K 35/741* | (2015.01) |
| *A61K 9/20* | (2006.01) |
| *A61K 36/185* | (2006.01) |
| *A61K 9/48* | (2006.01) |
| *A61K 9/00* | (2006.01) |
| *A23L 33/135* | (2016.01) |
| *A23L 33/21* | (2016.01) |
| *A23L 33/105* | (2016.01) |
| *A23P 10/30* | (2016.01) |
| *C12N 1/20* | (2006.01) |
| *A61K 31/352* | (2006.01) |

(52) U.S. Cl.
CPC .............. *A61K 9/20* (2013.01); *A23L 33/105* (2016.08); *A23L 33/135* (2016.08); *A23L 33/21* (2016.08); *A23P 10/30* (2016.08); *A61K 9/0053* (2013.01); *A61K 9/48* (2013.01); *A61K 36/185* (2013.01); *C12N 1/20* (2013.01); *A61K 31/352* (2013.01)

(58) Field of Classification Search
CPC .................................................... A61K 35/741
See application file for complete search history.

(56) References Cited

PUBLICATIONS

Gandolfi et al., "Hemp hurds biorefining: a path to green L-(+)-lactic acid production," Bioresource Technology 191:59-65, 2015.*

* cited by examiner

*Primary Examiner* — Rosanne Kosson
(74) *Attorney, Agent, or Firm* — Barbara E. Johnson, Esq.

(57) ABSTRACT

The present invention is a cannabidiol oral dosage form including predominantly or exclusively bacterially fermented hemp pomace, compounded as a tablet or formulated within a capsule generally without the addition of synthetic excipients, fillers or other additives, not including the inevitable presence of some moisture. The dosage forms contain dietary fiber, important to activity as the desired delivery system, having a ratio of one part soluble dietary fiber to 30 parts insoluble dietary fiber and delivers desirable/non hallucinogenic cannabinoids (CBD, CBG, etc.) in a ratio of 60:1 up to 120:1 to hallucinogenic cannabinoids (THC).

6 Claims, No Drawings

US 11,547,669 B2

INDIGENOUS AND IMPROVED BACTERIALLY FERMENTED CBD, CBG AND RELATED CANNABINOID ORAL DOSAGE FORMS

CROSS-REFERENCE TO RELATED APPLICATIONS

This patent application claims priority to, and incorporates herein by reference, U.S. Provisional Patent Application 62/912,930 filed 9 Oct. 2019, and is also a Continuation-in-Part of U.S. Ser. No. 16/781,489, filed 4 Feb. 2020.

FIELD OF THE INVENTION

The invention pertains to improved CBD (and related cannabinoid) delivery methods and dosage forms, namely, bacterially fermented hemp pomace.

BACKGROUND OF THE INVENTION

*Cannabis indica, Cannabis sativa* and *Cannabis ruderalis* have had a long history, from very early human horticulture. From thousands of years ago, to more recent prescriptions by Queen Victoria's physician, to the 2018 Farm Bill, there is a growing awareness everywhere of the power and strength of cannabinoids as active agents. At the same time, bacterial fermentation of comestibles of all kinds, including but by no means limited to Lactobacillus, has a comparably august history, and bacterial fermentation is so central to modern well-being that it is easy to lose sight of how ubiquitous comestible bacteria are. Life without cheese, buttermilk, kefir, yogurt, kim chi, sauerkraut, fermented legumes, wine, and beer, just to name a few, would have been as unthinkable, hundreds of years ago, as it is today—and of course all of these things rely on bacterial fermentation for their sheer existence.

While bacterial fermentation in the food and beverages industries has enjoyed a seemingly mature—or at least multiple-centuries-old-implementation in Western culture and economics, the relatively recent legality of hemp growing especially in the United States has led to a predictable avalanche in the cannabis industry much more recently. *Cannabis* extraction, formulation and processing in the United States, with legal avenues thanks to the 2018 Farm Bill, now regularly yield cannabidiol—CBD—and a myriad of products containing it. As a result, more-retail-cash-registers-than-not offer various CBD products for sale—sometimes many edible offerings such as individually wrapped chocolates containing CBD along with CBD topicals, oils and capsules—and of course online sales are brisk as well. CBD has long been known for its pain relieving, relaxing, sleep supporting, anxiety reducing benefits, rather than intoxicant properties, and sales of CBD containing products have been understandably swift and growing in the U.S. from 2018 to date.

As with any newly popular ingredient, there are opportunities for high quality products as well as those of lesser value and benefit. There are currently reliable, responsible cannabinoid rich hemp growers, manufacturers and, presumably, also formulators and peddlers reminiscent of the "snake oil salesmen" of the American 1800s. Chinese snake oil was a legitimate anti-inflammatory substance for decades if not centuries, prior to fake iterations that appeared later in the U.S. The original Chinese snake oil was made from the oil of the Chinese water snake, which was rich in the omega-3-fatty acids that are known to reduce inflammation. This "snake oil" in its original form was indeed effective as a topical medicament to treat arthritis and bursitis and, eventually, the putative product made its way to the United States—if not the omega-3-rich water snake itself, or its curative extract. The point here is that with CBD, as with anything else, responsible sourcing, processing and quality control in manufacturing are the bedrock of any superior pharmaceutically active agent. The pressures of manufacturing in light of a population clamoring for CBD are particularly intense, in world in which side-effect- or addiction-minimized pain management is still an elusive if (not scandal-laden) goal.

It is interesting that, as a general practice regarding naturally-occurring active agents—and particularly those of herbal sources—there seems to be a knee-jerk compulsion to extract the active agent compound from its botanical herb or spice. Extracting and synthesizing digitalis from foxglove, a natural herb, is of course a paradigm in pharmaceutical history. In theory there is nothing wrong with extraction processes—although in practice there can indeed be negative implications to extraction, in particular as to the molecule(s) to be extracted. Extraction agents such as petroleum or coal-tar derived solvents can create residues or even alter the chemical composition of the sought-after molecule. Worse, beneficial co-factors present in the natural product in this case an herb can be separated from the active agent so as to lose the synergy of administration of the whole herb with it's known and yet-to-be discovered compounds. Even today, when *Cannabis indica, Cannabis sativa* and *Cannabis ruderalis* are on the brink of becoming "health food" [so to speak] instead of "Just Say No!" fodder, the temptation seems to be ubiquitous to extract and isolate key constituents within them, in order to obtain their active agent(s) for further commercialization. The question which the present inventor asked, though, was—whether traditional extraction or isolation is the only processing method that can deliver the true benefits of hemp? And, if extraction or isolation is not the best approach, what additional beneficial conversions are possible to enhance the power and constituency of hemp for nutritional and dietary supplementation?

SUMMARY OF THE INVENTION

The present supplement, and pharmaceutical, nutraceutical and treatment method and method for delivering an active agent, centers on a powdered form of a previously bacterially fermented hemp pomace containing cannabinoids including CBD, dietary fiber of a particular ratio, vitamins, minerals, flavonoids, terpenes, fatty acids and amino acids, which powder is blended with other botanical ingredients or compressed into a tablet form for administration to or consumption by an animal or human in need of a reliably sourced CBD (or other cannabinoid) oral dosage form. Fermentation is conducted with any bacterium suitable for consumption or oral administration, including but not limited to *Bacillus subtilis, Bacillus subtilis* ssp *Natto, Bacillus coagulans, Lactobacillus plantarum. Acetobacter pasteurianus, Acetobacter ghanensis, Komagataeibacter oboediens,* or *Komagataeibacter saccharivorans,* used alone or in combination in any given culture. Such a dosage form containing the inventive powders retains live bacteria from the fermentation, as a probiotic fraction of the dosage form, as well as a retained minor fraction of water (moisture). While the present bacterially fermented hemp pomace is well suited for use alone, it may be admixed with other ingredients, whether active agents or excipients, fillers or comestible ingredients comprising dietary supplements or functional food ingredients. As a starting material, "spent extracted hemp biomass" is a co-product of cannabinoid (CBD, CBG etc) extraction—preferably an organic process without the use of toxic solvents or their derivatives. As with all extraction methods and the limited yields one can expect from an extraction process, in fact there is a sizeable fraction of cannabinoids (CBD) remaining in hemp pomace. Even more importantly, however, the CBD/cannabinoid(s) in the hemp pomace contain naturally occurring co-factors, known and currently unknown, including without limitation other cannabinoids, dietary fiber, fatty acids, amino acids, terpenes and flavonoids, which enhance any or all of delivery, bioavailability and efficacy of the CBD/cannabinoid(s) in vivo. This invention takes the spent extracted hemp pomace and subjects it to bacterial fermentation, both for the creation of a probiotic profile in the resulting end product but also beneficially to convert and enhance the constituent molecules and compounds in the hemp pomace to an increasingly diverse and prized spectrum of nutrients and active agents. A key part of the present invention therefore inheres in the synergy achieved by using "spent extracted hemp pomace" as the starting material for a bacterial fermentation, and then using the fermentation product as a further constituent, usually powdered, in a tablet or capsule (or equivalent) ingredient as a CBD/cannabinoid oral dosage form. Drying techniques are used which do not denature the constituent fraction or the bacteria, usually at low heat and controlled moisture. Another key component to the invention is in the engineering of the delivery system, with a beneficial soluble dietary fiber (SDF)/insoluble dietary fiber (IDF) ratio, in the "spent extracted hemp pomace" itself, of 1:30 SDF/IDF, allowing for effective formulation and delivery of key constituents. The process of creating hemp pomace using natural, non toxic forms of extraction, and subsequent bacterial fermentation, tend to increase the ratio (increasing the percentage) of non hallucinogenic/addictive cannabinoids such as CBD, CBG, CBC to hallucinogenic/addictive cannabinoids, i.e. THC. For example, many native hemp species have a ratio of CBD:THC of 20:1, whereas the process of producing spent extracted hemp pomace in accordance with this invention results in a CBD:THC ratio of between 60:1 to as high as 120:1, even apart from the converting effects by the bacterial fermentation.

DETAILED DESCRIPTION OF THE INVENTION

As with popular or over-the-counter dosage forms, particularly for active agents known to control pain, dosing is tantamount to safe and effective treatment. When it comes to CBD, general dosing guidelines suggest that a good starting dose is somewhere in the range of 1-5 mg once or twice a day, for an averaged sized human patient, with possible ethical dosing of up to 20 mg or more taken as often as three times per day. Veterinary dosing is generally pro rata by body mass/weight. As the CBD industry matures, inevitably further dosing guidelines will become available—but as with all active agents a serious challenge is to prevent inadvertent (or intentional) overdose. One benefit of the present formulations inheres in the lower cannabinoid (i.e. CBD) concentration of hemp pomace along with synergistic co-factors which provides a more balanced, "whole food" effect with less chance of deleterious side effects. A simultaneous benefit of the hemp pomace is that, whereas the CBD (or other cannabinoid) content has been reduced compared to the native hemp, the ratio of soluble dietary fiber (IDF) to insoluble dietary fiber remains the same as in the native hemp. This SDF/IDF ratio is 1:30, that is, for every 1 part of soluble dietary fiber in the hemp pomace, there is also 30 parts insoluble dietary fiber. This SDF/IDF ratio is discussed further, below. For the purposes of this specification, "hemp pomace" and "spent extracted hemp pomace" should be understood to be synonyms.

Even though the bacterially fermented hemp pomace of the invention, as discussed above, is the co-product of cannabinoid (CBD) extraction, this does not mean that it does not still contain meaningful amounts of cannabinoids, such as CBD. In the analogous case of wine making, after pressing of the fermented grapes, a large portion of the beneficial, natural compounds—such as resveratrol—remain in the grape pomace as has been detailed in published research and prior art. The importance of this analogy is that even hemp pomace resulting from a natural extraction process can be relatively rich in cannabinoids such as CBD, that is, contains on the order of 10-25% or so of the original CBD content of the pre-extraction "native" hemp biomass. All of this can be simply controlled by process monitoring and testing well known in the art.

The importance of the previous paragraph has to do with unit dosage form preparation of hemp pomace. If hemp has, for example, a starting content of 10% CBD, removal of 75-90% of that amount of CBD will yield (say) a 1-2.5% CBD content in the hemp pomace. This means that for every gram of hemp pomace (prior to bacterial fermentation), the intrinsic remaining CBD in the hemp pomace is on the order of 10-25 mg, which is right in the range of a standard unit dosage form and dosing amount. These levels are theoretical and can be monitored and adjusted in real life manufacturing settings. For illustrative purposes, then, if a gram of hemp pomace contains 15 mg of CBD, it is readily possible to formulate 1 mg, 3 gm, 5 mg, 10 mg and even 20 mg CBD dosage forms by selecting the appropriate fraction of a gram of hemp pomace, or possibly slightly more than one gram, per unit dosage form. Larger serving sizes of tablets or capsules can thus contain up to 20 mg CBD while still having a size that can be consumed without difficulty. In addition, bacterial fermentation increases the presence of cannabinoid by 12-300% (see Example 3) so the 1-2.5% cannabinoid before bacterial fermentation becomes 1.1-7.5% cannabinoid in the fermented pomace, but the ability of hemp pomace with bacterial fermentation to be formulated into oral dosage form capsules—or to be tabletted directly—means that creation of dosing per unit is within the skill of the art. The combination itself, of taking spent extracted hemp pomace and fermenting it with bacteria prior to creating one or more dosage forms from the fermentation product, is the gravamen of the present invention.

As set forth above, the present spent extracted hemp pomace is fermented with any suitable bacterium, including but not limited to *Bacillus subtilis, Bacillus subtilis* ssp *Natto, Bacillus coagulans*, and *Lactobacillus plantarum*. The presence of this probiotic and its fermentation product (and viable cultures) is the main exception, besides moisture, to the premise that, overall, the dosage form material (apart from a capsule if necessary) is predominantly or completely hemp pomace. In other words, except for further formulations in functional foods and other products in which the present fermented product can be an ingredient, it is important to recognize the versatility—and even the conformability for tabletting and the like—of just the bacterially fermented native extracted hemp pomace that is subsequently gently dried and comminuted—without need for a lot more processing or formulation as so many other active agents typically do need.

It almost goes without saying that organically sourced hemp, extracted without hydrocarbon-based or petroleum or coal tar derived solvents, is the best choice for the native extracted hemp pomace starting material according to the present invention. By using organic hemp and avoiding noxious extraction solvents, the presence of pesticides or other solvent residues or undesirable adulterants in the hemp pomace is reduced to a beneficial minimum. Not only is the reduction of these extraneous contaminants good in and of itself, but the absence of unwanted residues maximizes the original confluence of the indigenous cannabinoids such as CBD with its synergistic co-factors, known (see list above) or unknown.

Bacterially fermented hemp pomace according to the present invention is typically dried, possibly "activated" through de-carboxylation and co-minuted prior to tabletting or encapsulating. Dehydration to a moisture content of below 15%, preferably below 10% and more preferably to 5-6% is important in the creation of the present oral dosage forms. The co-minution may be but need not be to a (small) particle size generally within the range of powders. Generally speaking, bacterially fermented hemp pomace particles of at least 100 microns in diameter, up to irregularly shaped particles of up to about 5 mm in their longest dimension, are best for tabletting or encapsulating according to the present invention. Surprisingly, hemp pomace particles of this size are beneficially self tabletting without added ingredients and with a minimum of compression energy, that is, not enough pressure to generate significant heat. Avoidance of excessive processing also prevents the generation of unwanted heat that can denature cannabinoids (CBD), terpenes or additional cofactors in the hemp pomace. Having said that, however, the administration of hemp pomace as a powder (that is, in traditional powder particle size distributions smaller than 100 microns) and as predominantly the only oral dosage form constituent as described above—is still within the scope of the present invention.

The primary disclosure of this patent application is directed to dosage forms in which—with few exceptions such as added inert excipients, probiotics, botanicals, vitamins and minerals or adjusted or retained moisture—bacterially fermented hemp pomace is the main ingredient in an oral dosage form. Having said that, there is a specialized application for hemp pomace, with or without probiotic, as a non-predominant dosage form additive, that is, as an excipient, usually as a hardening agent. The properties of hemp pomace are so advantageous for oral dosage form preparation that, even apart from the main embodiment of the invention in which hemp pomace is administered predominantly by itself, hemp pomace is also uniquely useful as a hardening agent and excipient for other oral dosage forms. The hemp pomace used as a hardening agent or pharmaceutical excipient may be employed with or without fermented, or co-formulated, probiotic, such as bacteria or fungus. By the same token, the emphasis in the present disclosure is on bacterially fermented spent extracted hemp pomace, for all the benefits above described, and yet it is equally possible to ferment, or co-formulate, native hemp (that is, not previously extracted) with bacterial (and even fungal) ingredients to achieve similar formulational benefits. One skilled in the art is well able to adjust the dosing parameters discussed above to accommodate the higher constituent amounts, such as CBD, in the native hemp versus the hemp pomace.

As disclosed above, hemp pomace (prior to bacterial fermentation) contains total dietary fiber (TDF) having a ratio of 1 part SDF to 30 parts IDF. As compared to higher SDF-containing botanicals, such as for example oat bran or bananas, a ratio of 1:30 SDF/IDF is a notably low SDF/IDF ratio and, for the purposes of the present invention, this high inclusion of IDF is extremely beneficial to delivery of CBD and other cannabinoids from an oral dosage form. SDF, upon oral administration, tends to create a sol/gel in the gastrointestinal tract, which in turns tends to retain in solution, i.e. binding or suspension, other molecules in its vicinity such as, in this case, cannabinoids. In other contexts, SDF is a highly desirable nutrient, that can even be partially digested by bacteria in the gut, but in the context of a cannabinoid delivery system SDF actually creates a binding system and subsequent removal from the body for an active agent, rather than a true delivery (release) system into the blood stream. By contrast, the high IDF inclusion assures the desirable release of the active agent promptly if not instantly in the stomach or upper gastrointestinal tract. Given this understanding of how the present oral dosage form works, moreover, it may be seen that the present oral composition, although botanical in initial source, is a highly engineered composition and not merely a product of nature at all. With the present oral dosage forms, the cannabinoid content is reduced (compared to native hemp) and yet the SDF/IDF ratio of 1:30, typical of native hemp, enhances delivery due to its high soluble fiber fraction. In fact, the engineering of the hemp into pomace creates a fascinating paradigm—when one realizes both that extraction is NOT always the desired processing and delivery method for hemp and that native hemp may be too high in THC content to be optimally useful as an oral dosage form, hemp pomace becomes a primary, premium product, and in no way a by-product of something else. (Even more interesting, in a world full of controlled-release and sustained-release pharmaceuticals, is the effective "flip" of the controlled release paradigm in the present invention, in that with the present invention the active agent delivery is designed to be instantaneous or at least prompt (not controlled or sustained), but the dosing per unit is deliberately reduced from its native form, rather than concentrated.) With the above understanding, therefore, the following terms are all synonymous: spent hemp pomace; hemp pomace, extracted pomace; extracted biomass; extracted hemp biomass; extracted hemp marc, extracted marc, native marc and native pomace. Moreover, inasmuch as the pomace is the supportable star of hemp extraction, in contrast to an extract, it is appropriate to call the present pomace "Hemp Extract" or "Whole Food Cannabinoid Extract," in the sense that it is the pomace that has been importantly wrested from the native hemp, not the relatively less useful traditional cannabinoid extraction products.

Important cannabinoids in hemp pomace are not limited to cannabidiol (CBD). Known significant cannabinoids other than THC include, without limitation, cannabigerol (CBG), cannabidivarin (CBDV), cannabichromene (CBC), cannabinol (CBN) and combinations thereof. Various strains of hemp tend to present different ratios of these cannabinoids and, in due course, the desired ratios will also inevitably be genetically engineered if not traditionally cross-bred. The ability of hemp pomace to serve as a uniquely effective delivery system for any and all cannabinoids and additional beneficial hemp components, typically in reduced amounts compared to their native hemp percentages, will apply to any hemp strain known or developed in the future.

A number of interesting and beneficial things happen to spent extracted hemp pomace when it is subjected to bacterial fermentation. Unlike with fungal fermentation of spent extracted hemp pomace, in which the pomace inevitably has to be sterilized prior to funguculture, bacterial fermentation provides its own de facto sterilization (by competitive overgrowth dynamics) so that constituents of the pomace that are particularly desirable are not denatured due to excessive heating. An example is terpenes—which are plentiful in non-heat-treated spent extracted hemp pomace and do not disappear before or during bacterial fermentation. Therefore, bacterial fermentation can be applied to either hemp pomace that has gone through a decarboxylated process (typically heat and pressure) or a hemp pomace that is raw and unheated. Bacterial fermentation also creates metabolites with the substrate such as organic acids (acetic, malic, formic . . . ) which contribute to nutritive and active agent profiles and constituent diversity. Perhaps most important of all, fermentation of hemp pomace with bacterial culture preserves and stabilizes the cannabinoid acids (CBDA, CBGA etc) in the hemp pomace, which is important in preserving the anti-nausea, anti-withdrawal symptom and pain management aspect of cannabinoid acids (un-de-carboxylated) themselves. Of course having all these benefits together with a novel probiotic makes for a much needed, new and useful composition, for administration in unit dosage form.

EXAMPLE 1

A quantity of native hemp is subjected to a traditional extraction of cannabinoids by moderate crushing and extraction of cannabinoids to create a "hemp pomace" which continued to include cannabinoids therein. The extraction may be by ethanol solvent extraction, carbon dioxide solvent extraction, vapor distillation, or flash pasteurization. At this writing, such extraction techniques for hemp (Cannabis) are known by those skilled in the art. The resulting pomace is carefully air dried at temperatures lower than 115 degrees Fahrenheit to prevent denaturing of all compounds and compositions in the pomace. A representative dried pomace prepared according to the above method steps contained 6% moisture and certain exemplary specifications listed in the below table. The dried pomace was divided and manufactured into compressed tablets to contain 1 gram by weight.

TABLE I

| QD252-Protein-Combustion | Reference | Accreditation | Analysis Completed |
|---|---|---|---|
| | AOAC 990.03; AOAC 992.15 | A2LA ISO/IEC 17025: 2005 | Jan. 15, 2020 |
| Parameter | Result | | |
| Protein | 26.50% | | |
| Nitrogen-Combustion | 4.24% | | |
| Protein Factor | 6.25 | | |
| QD250-Ash | Reference | Accreditation | Analysis Completed |
| | AOAC 942.05 | A2LA ISO/IEC 17025: 2005 | Jan. 15, 2020 |
| Parameter | Result | | |
| Ash | 17.74% | | |

TABLE I-continued

| QD226-Calories, Calculated | Reference | Accreditation | Analysis Completed |
|---|---|---|---|
| | CFR-Atwater calculation | A2LA ISO/IEC 17025: 2005 | Jan. 17, 2020 |
| Parameter | Result | | |
| Calories Calculated | 323 kcal/100 g | | |
| QD038-Carbohydrates, | Reference | Accreditation | Analysis Completed |
| | CFR 21-calc. | A2LA ISO/IEC 17025: 2005 | Jan. 17, 2020 |
| Parameter | Result | | |
| Carbohydrates, Calculated | 46.25% | | |
| QD148-Moisture by Vacuum | Reference | Accreditation | Analysis Completed |
| | AOAC 925.09 | A2LA ISO/IEC 17025: 2005 | Jan. 17, 2020 |
| Parameter | Result | | |
| Moisture and Volatiles-Vacuum Oven | 6.0% | | |
| QD251-Calcium by ICP | Reference | Accreditation | Analysis Completed |
| | AOAC 984.27 mod, 927.02 mod | A2LA ISO/IEC 17025: 2005 | Jan. 15, 2020 |

EXAMPLE 2

A quantity of spent extracted hemp pomace (1 kilogram) was admixed and further extracted in situ with a raw *Acetobacter* culture as follows. A standard vinegar "mother" disc of viable Acetobacter suspended in a cellulose disc, approximately 4 ounces, was mixed with the spent extracted hemp pomace and allowed to incubate for 100 hours at 100 degrees F. The co-fermented ingredients were not separated, and were dried and formulated into particulates (powders) for inclusion in oral dosage form nutritional supplements. By testing and titrating, each unit dosage form contained approximately 425 mg of CBD per serving.

EXAMPLE 3

Six samples of an activated hemp composition, all of the same mass, were individually autoclaved at 170 degrees F. for four hours, 170 degrees F. for two hours, 200 degrees F. for four hours, 200 degrees F. for two hours, 250 degrees F. for four hours and 250 degrees F. for two hours. The hemp starting material contained 75% native hemp and 25% of a noncannabinoid spice mix that was uniform throughout the tests conducted and reported in this example. After the autoclaving step, expected to accomplish at least partial decarboxylation of organic acids in the hemp material including cannabinoid acids, the cannabidiol, cannabidiol acid and total constituency of the autoclaved hemp material was measured and is shown in the following table as to the six described samples.

TABLE II

| Sample No. | CBD % | CBDA % | Total CBD + CBDA % |
|---|---|---|---|
| 1 | 1.95 | 0.73 | 2.60% |
| 2 | 3.1 | 1.01 | 4 |
| 3 | 5.4 | 0.19 | 5.6 |
| 4 | 5.4 | 0.47 | 4.8 |
| 5 | 5 | non-detectable | 5 |
| 6 | 6.1 | non-detectable | 6.1 |

Samples identical to 1-6 after autoclaving were relabelled Samples 7-12 and were inoculated and incubated with *Acetobacter*, under identical inoculation and incubation parameters for all samples. After incubation, the CBD, CBDA and total combined CBD+CBDA constituencies were measured and reported as shown in the following table.

TABLE III

| Sample No. | CBD % | CBDA % | Total CBD+ CBDA % |
|---|---|---|---|
| 7 | 6.3 | 3.2 | 9.10% |
| 8 | 2.2 | 2.4 | 4.4 |
| 9 | 6.1 | 0.32 | 6.3 |
| 10 | 6.2 | 0.5 | 6.6 |
| 11 | 7.1 | non-detectable | 7.1 |
| 12 | 9.3 | non-detectable | 9.3 |

The above data (eliminating the outliers) illustrate that it is possible to increase individual CBD or CBDA constituents, or the combination of the two, by about a twelve percent increase up to about a 300% increase simply by the bacterial fermentation of the cannabinoid starting material.

Although the technology has been described with particularity above, with reference to specific materials and methods, the invention is only to be limited as is set forth in the following claims.

I claim:

1. A cannabinoid oral dosage form in unit dosage form, consisting essentially of bacterially fermented hemp pomace, compounded as a tablet or within a capsule, powder or other unit dosage form as the predominant or exclusive ingredient, having a soluble dietary fiber to insoluble dietary fiber ratio of 1:30, having a maximum cannabinoid dose per unit dosage form of 25 mg, and having viable bacteria therein as a probiotic dietary supplement.

2. The oral dosage form of claim 1, wherein each oral dosage form contains less than 10% water and wherein said cannabinoid is selected from the group consisting of cannabidiol, cannabigerol, cannabidivarin, cannabichromene, cannabinol and a combination thereof.

3. The oral dosage form of claim 1, wherein said hemp pomace is fermented with one or more bacteria selected from the group consisting of *Bacillus subtilis, Bacillus subtilis* ssp *Natto, Bacillus coagulans, Lactobacillus plantarum, Acetobacter pasteurianus, Acetobacter ghanensis, Komagataeibacter oboediens,* and *Komagataeibacter saccharivorans* prior to compounding.

4. The oral dosage form of claim 1, wherein said dosage form contains no more than 10 mg cannabinoid per unit dosage form.

5. The oral dosage form of claim 1 wherein said cannabinoid is present at a level of between 12 and 300% greater than a starting level of said cannabinoid due to the action of bacterial fermentation on same pomace.

6. The oral dosage form of claim 5 wherein said cannabinoid is present in the amount of 1.1-7.5% in said hemp pomace.

* * * * *